(12) United States Patent
Groke et al.

(10) Patent No.: US 9,555,263 B2
(45) Date of Patent: Jan. 31, 2017

(54) APPARATUS, SYSTEM AND METHOD FOR SUPPORTING A BRACHYTHERAPY

(71) Applicant: Siemens Aktiengesellschaft, München (DE)

(72) Inventors: David Groke, Nürnberg (DE); Michael Wiets, Erlangen (DE)

(73) Assignee: SIEMENS HEALTHCARE GmbH, Erlangen (DE)

(*) Notice: Subject to any disclaimer, the term of this patent is extended or adjusted under 35 U.S.C. 154(b) by 0 days.

(21) Appl. No.: 13/970,710

(22) Filed: Aug. 20, 2013

(65) Prior Publication Data

US 2014/0058187 A1 Feb. 27, 2014

(30) Foreign Application Priority Data

Aug. 27, 2012 (DE) .................. 10 2012 215 170

(51) Int. Cl.
*A61N 5/10* (2006.01)

(52) U.S. Cl.
CPC ........... *A61N 5/1001* (2013.01); *A61N 5/1071* (2013.01)

(58) Field of Classification Search
CPC .. A61N 5/1071; A61N 5/1075; A61N 5/1001; A61N 5/1048; A61N 2005/1072; A61N 5/1031; A61N 5/1064; A61N 5/1067; A61N 5/1077; A61N 5/10; A61N 5/1027; A61N 2005/1008; A61N 2005/1019; A61N 2005/1021; A61N 2005/1024; A61N 2005/1054; A61N 2005/1055; A61N 2005/1059; A61N 2005/1061; A61N 2005/1062; A61N 2019/542

See application file for complete search history.

(56) References Cited

U.S. PATENT DOCUMENTS

| | | | | |
|---|---|---|---|---|
| 5,851,172 | A * | 12/1998 | Bueche et al. | 600/7 |
| 7,662,083 | B2 | 2/2010 | Gueye | |
| 9,199,093 | B2 | 12/2015 | Brusasco et al. | |
| 2001/0027260 | A1* | 10/2001 | Uematsu | A61N 5/1048 600/1 |
| 2005/0101824 | A1 | 5/2005 | Stubbs | |
| 2006/0241332 | A1* | 10/2006 | Klein et al. | 600/1 |
| 2012/0232324 | A1* | 9/2012 | Brusasco et al. | 600/1 |

FOREIGN PATENT DOCUMENTS

| | | |
|---|---|---|
| CN | 1814321 A | 8/2006 |
| CN | 101496018 A | 7/2009 |
| CN | 102083498 A | 6/2011 |
| EP | 1316330 A1 | 6/2003 |
| WO | WO 2007079226 A2 | 7/2007 |

\* cited by examiner

*Primary Examiner* — Christine H Matthews

(57) ABSTRACT

An apparatus for supporting a brachytherapy includes at least one radiation device, at least one dose measuring device, and a processing unit. The at least one dose measuring device is configured to be introduced into a target area of an object under treatment which includes at least one target object and that is designed to measure radioactive radiation originating from the at least one radiation device, which is introduced into the target area of the object under treatment, and to provide the measured values by way of a device for transmission to the processing unit.

5 Claims, 3 Drawing Sheets

APPARATUS, SYSTEM AND METHOD FOR SUPPORTING A BRACHYTHERAPY

CROSS REFERENCE TO RELATED APPLICATIONS

The present application claims priority to German Patent Office application No. 102012215170.2 DE filed Aug. 27, 2012, the entire content of which is hereby incorporated herein by reference.

FIELD OF INVENTION

The present invention relates to an apparatus and a system for supporting a brachytherapy. In addition the present invention relates to a corresponding method for supporting a brachytherapy.

BACKGROUND OF INVENTION

Brachytherapy involves a minimally-invasive method for radiation therapy of a tumor, e.g. a prostate carcinoma, a cervix carcinoma, a mammary carcinoma or a larynx carcinoma by means of internal radiation therapy or radiation treatment in a direct target region. To carry out the therapy one or more radiation sources is placed in the direct vicinity of the area to be radiation-treated. To introduce the radiation sources, what are referred to as applicators or guides are frequently used, which are apparatuses similar to a catheter which are introduced or implanted into the body close to the tumor or directly into the tumor tissue. The radiation sources, in what is referred to as temporary brachytherapy, can remain in the body temporarily, e.g. for a few minutes or hours, or in permanent brachytherapy over a longer period or for an unlimited time.

In order to determine the precise target position of the radiation sources, a computed tomography (CT) or magnetic resonance tomography (MRT) image of the region to be irradiated can be prepared for example prior to the therapy. With the aid of this dataset obtained the precise dose distribution in the target region is calculated on a radiation therapy planning system. The number and the positions of the applicators to be introduced and the radiation sources are determined with reference to the ideal dose distribution on or in the tumor. Dose planning means that the radiation is only applied in high doses where the tumor is located. Through this method the surrounding and in some cases very highly radiation-sensitive tissue is not unnecessarily irradiated and damage is minimized. In addition, by contrast with an external radiation therapy, the skin is not damaged since radiation therapy is from inside.

After a preliminary examination, dose planning and the procurement of the materials needed, the actual brachytherapy is carried out. For this purpose the patient is sedated or anesthetized in a sterile environment (OP) and the applicators are implanted. This can be done using 2D fluoroscopy. After successful checking of the position of the applicators the internal radiation treatment is carried out with the aid of radioactive radiation sources, so-called seeds, e.g. in the form of capsules of Cesium-137 between one and five mm long. In the so-called afterloading method, the seeds are introduced manually or automatically through the applicators into their target area, in stages if necessary. The radiation dose in the target area is calculated using the radiation intensity of the individual seeds to be expected, as well as the time that they are in the applicator or in the target area. When the predicted exposure time is reached, in the case of a temporary brachytherapy, the seeds and the applicators are removed again, if necessary in stages. The exposure time as well as the calculated applied dose can be documented.

SUMMARY OF INVENTION

The object of the present invention is now to specify an apparatus and a system for supporting a brachytherapy which make it possible to increase the effectiveness of a brachytherapy compared to known brachytherapies. It is also an object of the invention to describe an associated method.

The invention achieves this object with an apparatus for supporting a brachytherapy with the features of the first independent claim, a system for supporting a brachytherapy with the features of the second independent claim and a method for supporting a brachytherapy with the features of the third independent claim.

The basic idea behind the invention is an apparatus for supporting a brachytherapy having at least one dose measuring means which is able to be introduced into a target area of an object under treatment comprising at least one target object. The dose measuring means is designed to measure radioactive radiation of at least one irradiation means which is introduced into the target area of the object under treatment and to provide the measured values by means of the transmission means to a processing unit.

The inventive apparatus for supporting a brachytherapy thus comprises at least one dose measuring means which can be introduced into a target area of an object under treatment, wherein the target area comprises at least one target object. An object to be examined is to be understood as a human or animal patient for instance on which a brachytherapy is to be carried out. The object under treatment has a target area or a target region, i.e. a spatial area comprising a target object, for example a tumor to be treated. The at least one dose measuring means is designed to measure radioactive radiation, wherein the radioactive radiation essentially originates from at least one radiation means which is introduced into the target area of the object under treatment. The radiation means can involve radioactive radiation sources, the seeds, e.g. in the form of capsules around one to five mm in length, consisting of a radionuclide, for example cesium-137, cobalt-60, iridium-192, iodine-125, Palladium-103 or Ruthenium-106, or also a miniaturized low-energy x-ray emitter. The dose measuring means is also designed to provide the measured values obtained to a processing unit by way of a transmission means. The dose measuring means can for example involve a dose measuring chamber known per se, preferably miniaturized, or a radiation or particle detector, which can transfer measured values obtained to a processing unit, e.g. a computer, wherein the transmission is undertaken by means of the transmission means which can be embodied as a wired or wireless connection. With the aid of the dose measuring means the radiation emitted by the radiation means in the vicinity of the object under treatment can thus be measured directly, in order in this way, by contrast with the radiation distribution only predicted in previous methods, to guarantee a more precise dose application and dose monitoring.

In an advantageous development the at least one dose measuring means is able to be disposed on or in at least one wire-type or hose-type retaining means.

To enable the dose measuring means to be easily introduced into the target area, wire-type or hose-type retaining means are advantageous for accommodating the dose measuring means. A hose-type retaining means can take the form of a catheter or a cannula, a wire-type retaining means can take the form of a guide wire or a needle. In such cases different arrangements are conceivable, such as for example a dose measuring means on a wire-type or hose-type retaining means, a number of dose measuring means on one, one does measurement means in each case on one or several dose measuring means on a number of wire-type or hose-type retaining means.

In a further advantageous embodiment a dose measuring means is able to be disposed on the tip of the wire-type or hose-type retaining means.

In this embodiment one of the at least one dose measuring means is able to be disposed at the tip of the wire-type or hose-type retaining means. This makes possible for example the measurement of radioactive radiation in the direction of the longitudinal axis of the wire-type or hose-type retaining means. This arrangement can also offer mechanical advantages, if the dose measuring means for example is able to be disposed like a screw closure on an end of the retaining means.

A further advantageous embodiment makes provision for the at least one dose measuring means to be disposed on or in an applicator.

As described at the start radiation sources such as seeds can be introduced into the target area with the aid of so-called applicators, i.e. in the vicinity of a tumor or even directly into the tumor tissue. Since with a temporary brachytherapy the applicators mostly remain during the radiotherapy in the body of the object under treatment, it is advantageous for the dose measuring means to be able to be disposed on or in an applicator or for these to be integrated into an applicator.

A further underlying idea of the invention relates to a system for supporting a brachytherapy. The system comprises at least one of the inventive apparatuses previously described for supporting a brachytherapy and a processing unit which is embodied to receive the measured values provided by the at least one apparatus.

The system of supporting a brachytherapy thus comprises, in addition to an inventive apparatus for supporting a brachytherapy, a processing unit, e.g. a computer or an electronic circuit, which provides the technical means for receiving the measured values of the radioactive radiation of the at least one radiation means determined and provided by the apparatus. Depending on transmission means, this can for example include input circuits for wired transmission technology, or receive circuits in the case of wireless transmission technology. In addition software which is necessary for the transmission can also be embodied on the processing unit.

In an advantageous development the processing unit is embodied to receive at least one threshold value and to compare it with at least one measured value provided by the at least one apparatus.

This feature of the system makes it possible to compare the measured values of the radiation dose which are caused by the at least one radiation means, with predeterminable threshold values. The predeterminable threshold values can be determined for example by measurement sequences or calculated by physical-mathematical models of the object under treatment and the characteristics of radiation means and dose means. The threshold values can for example specify values at which tissue is likely to be damaged. The receipt of the threshold value or threshold values can be undertaken for example by inputting at an input means such as a computer keyboard. Preferably the difference between measured radiation dose and threshold value is output for example at an output means, such as a computer monitor. It is further conceivable, if the threshold value is exceeded, for an optical and/or acoustic warning to be output to warn a user of the system for supporting a brachytherapy.

In a further advantageous embodiment the system comprises an imaging apparatus which is designed to obtain an image of the at least one radiation means, the at least one dose measuring means and the at least one target object and to provide them to the processing unit.

An imaging apparatus can for example be understood as an x-ray device, a computed tomography device, CT device or a magnetic resonance tomography device, MRT device. The image provided can preferably be presented on an output means such as a computer monitor, in order to give the user of the system an insight into the local position of radiation means, dose measuring means and target object.

In a further advantageous embodiment of the system for supporting a brachytherapy the computing unit is designed to determine the positions of the at least one radiation means, the at least one dose measuring means and the at least one target object from the image of the at least one radiation means, the at least one dose measuring means and the at least one target object, and to determine from the positions a spatial distribution of the radiation dose conditional on the at least one radiation means.

Using image processing algorithms known per se, especially for medical images, at least the position of radiation means, dose measuring means and target object can be determined from one or more images of the imaging device. A spatial distribution of the radiation dose which is conditional on the at least one radiation means can be determined from this. Preferably the duration of the radiation and/or the radiation power of the radiation means are included in the determination of the spatial distribution of the radiation dose. Especially advantageously the spatial distribution of the radiation dose is visualized on an output means, e.g. a computer monitor. For this purpose the values of the spatial distribution can be visualized by colors, wherein preferably green colors are used for a low radiation amount through to red colors for a high radiation amount. It is also a useful for the positions of radiation-sensitive organs to be known for the said objects and for their radiation load, possibly also weighted in accordance with their radiation sensitivity, to be determined and visualized. Through this presentation a user, e.g. a radiologist or oncologist, obtains a good insight into the effectiveness but also possibly critical arrangements during a brachytherapy.

A further underlying idea of the invention relates to a method for supporting a brachytherapy with one of the previously described inventive apparatuses, wherein the at least one dose measuring means is introduced into the target area of the object under treatment surrounding at least one target object, radioactive radiation of the at least one radiation means which is introduced into the target area of the object under treatment is measured and measured values are provided by means of the transmission means to the processing unit.

The basic idea of the inventive method for supporting a brachytherapy is thus based on a previously described apparatus for supporting a brachytherapy, which is already introduced into the target area of the object under treatment. Furthermore the at least one radiation means emitting radioactive radiation is also introduced into the target area. The method steps are finally measuring the radiation of the at least one radiation means and providing the measured values to a processing unit by way of the transmission means.

An inventive embodiment of a basic idea of the invention provides for the method for supporting a brachytherapy with a previously described system, wherein the at least one dose measuring means is introduced into the target area of the object under treatment surrounding at least one target object and the at least one radiation means is introduced into the target area of the object under treatment, comprising the following steps:

S1) Recording an image of the at least one radiation means, the at least one dose measuring means and the at least one target object with the aid of the imaging apparatus and transmission of the image to the processing unit;

S2) Determining the positions of the at least one radiation means, the at least one dose measuring means and the at least one target object;

S3) Measuring radioactive radiation of the at least one radiation means with the aid of the at least one dose measuring means;

S4) Determining the spatial distribution of the radiation dose conditional on the at least one radiation means.

In an advantageous development of the method the following method step, S5, is executed after method step S4:

S5) Comparing the spatial distribution of the radiation dose conditional on the at least one radiation means with a predeterminable spatial distribution.

Preferably the duration of the radiation and/or the radiation power of the radiation means are included in the determination of the spatial distribution of the radiation dose. Especially advantageously the spatial distribution of the radiation dose is visualized on an output means, e.g. a computer monitor. For this purpose the values of the spatial distribution can be visualized by colors, wherein preferably green colors are used for a low radiation amount through to red colors for a high radiation amount. It is useful if, for the said objects, the positions of radiation-sensitive organs are also determined and for their radiation load possibly to be weighted, determined and visualized also in accordance with their radiation sensitivity. Through this presentation a user, e.g. a radiologist or oncologist, obtains a good insight into the effectiveness but also possibly critical arrangements during a brachytherapy. The predeterminable spatial distribution of the radiation dose, by means of an input means for example, and comparison with the measured spatial distribution of the radiation dose, advantageously enables a predicted spatial distribution of the radiation dose to be checked. Furthermore areas, e.g. radiation-sensitive organs, can be allocated a low allowed radiation dose, which, if exceeded, is visualized on an output means, e.g. a computer monitor for instance.

In a further advantageous embodiment of the method at least the measurement of the radioactive radiation of the at least one radiation means is executed repeatedly, until an abort criterion is fulfilled.

An abort criterion can for example be the reaching of a predeterminable number of method passes, the reaching of a predeterminable duration or the actuation of a key, e.g. on an input means such as a computer keyboard, or the actuation of a switch. If the abort criterion is not fulfilled, at least the measurement of the radioactive radiation of the at least one radiation means is repeated.

A further advantageous embodiment makes provision for the method to be executed automatically.

An at least partly automatically executed method offers the advantage that few user activities are needed to execute the method.

The exemplary embodiments described in more detail below represent preferred embodiment variants of the present invention.

BRIEF DESCRIPTION OF THE DRAWINGS

Further advantageous developments emerge from the figures below along with their description, in which:

FIG. 1 shows a diagram for describing a brachytherapy according to the prior art. A brachytherapy for therapy of a target object 32, here a tumor, is performed on an object under treatment 30, here a human patient. To this end an applicator 35, here in the form of a catheter, is introduced into a target area 31. The target area 31 comprises at least one target object 32, i.e. the target area is generally a volume within the object under treatment 30, within which at least the target object 32 lies. By means of the applicator 35 a radiation means 33, referred to here as a seed consisting of a radionuclide for example Cesium-137, Cobalt-60, Iridium-192, Iodine-125, Palladium-103 or Ruthenium-106, also a miniaturized low-energy x-ray emitter is bought into the direct vicinity of the target object 32. The radiation means 33 emits high-energy radiation, indicated in FIG. 1 by lines 34 which penetrate the target object 32. A great advantage of brachytherapy is that the radiation effect involves a very limited region around the radiation source. Despite this tissue and organs in the vicinity of the radiation means 33 are still irradiated, so that the location of the introduction and the type of radiation means 33 and the duration of the treatment must be very well considered in order to minimize the health risks for the object under treatment 30.

FIG. 2 shows a diagram for describing an exemplary embodiment of a system 100 for supporting a brachytherapy. Once again a brachytherapy for radiotherapy of a target object 32, here a tumor, is carried out on an object under treatment 30, here a human patient. To this end an applicator 35, here in the form of a catheter, is introduced into a target area 31, which at least includes the target object 32. By means of the applicator 35 a radiation means 33, referred to here as a seed, consisting of a radionuclide, or also a miniaturized low-energy x-ray emitter, can be bought into the immediate vicinity of the target object 32. The radiation means 33 emits high-energy radiation, indicated in FIG. 2 by lines 34 which penetrate the target object 32. The system 100, which comprises an apparatus 1 for supporting a brachytherapy and a processing unit 20, here a computer, serves to support the brachytherapy. The apparatus 1 for supporting a brachytherapy comprises a dose measuring means 2 which is introduced into the target area 31 and which is designed to measure the radioactive radiation 34 of the radiation means 33 which is likewise introduced into the target area 31 of the object under treatment 30 and to provide the measured values by means of the transmission means 3, here connected via an electrical line, to the processing unit 20. With the aid of the dose measuring means 2 the radiation 34 emitted by the radiation means 33 can thus be measured directly in the vicinity of the object under treatment 32, in order to guarantee a more precise dose administration and dose monitoring compared to the radiation distribution only predicted in previous methods. The measured values are transmitted via the transmission means 3 to the processing unit 20 and can be further processed there, e.g. visualized.

FIG. 3 shows a schematic diagram of an exemplary embodiment of an apparatus 1' for supporting a brachytherapy. The apparatus 1' shown in this exemplary embodiment advantageously combines the function of an applicator with an inventive function for supporting a brachytherapy. The function of the applicator is guaranteed by the applicator 35, in this case a catheter-like apparatus, which can be introduced or implanted into a body close to a tumor or directly into the tumor tissue. A radiation means 33, here a seed consisting of a radionuclide which emits radioactive radiation 34, is used for radiotherapy. In the so-called afterloading method, the seeds are introduced manually or automatically through the applicators into their target area, in stages if necessary. A dose measuring means 2 is designed to measure radioactive radiation 34, wherein the radioactive radiation 34 originates essentially from the radiation means 33. The dose measuring means 2 is disposed at the tip of the applicator 35, which also serves as a retaining means. This makes it possible for example to measure radioactive radiation 34 in the direction of the longitudinal axis of the applicator 35. This arrangement also offers mechanical advantages, since the dose measuring means 2 is able to be attached like a screw closure to one end of the applicator 35. The dose measuring means 2 is also designed to provide the measured values obtained to a processing unit not shown in the figure, e.g. a computer, by way of a transmission means 3. The dose measuring means 2 can for example involve a miniaturized dose measuring chamber or a radiation or particle detector, which can transfer measured values obtained to the processing unit, wherein the transmission is undertaken by means of a transmission means 3, which is embodied here as a wireless transmission means for wireless data transmission. Naturally the processing unit not shown in the figure is equipped with a corresponding transmission means for receiving the measured values. With the aid of the dose measuring means 2 the radiation 34 emitted by the radiation means 33 can be measured directly in that the vicinity of the tumor to be treated and transferred to the processing unit. Thus a more precise dose administration and dose monitoring is guaranteed compared to the radiation distribution only predicted in previous methods.

FIG. 4 shows a schematic diagram of a further exemplary embodiment of a system 100 for supporting a brachytherapy with two different apparatuses 1 and 1' for supporting a brachytherapy. The apparatus 1' for supporting a brachytherapy comprises an applicator 35, i.e. an apparatus which is suitable for introducing a radiation means 33 which emits radioactive radiation 34 and two dose measuring means 2 and 2'. The dose measuring means 2 and 2' are designed to measure radioactive radiation 34, wherein the radioactive radiation 34 originates essentially from the radiation means 33. The dose measuring means 2 is disposed at the tip of the applicator 35, the dose measuring means 2' is disposed proximally, i.e. towards the body, on the applicator. The measured values of the dose measuring means 2 and 2' can be transmitted by wire via the transmission means 3 and 3' which are embodied as electrical lines, to the processing unit 20, which is embodied as a computer. The apparatus 1 for supporting a brachytherapy is not disposed on an applicator. To enable the dose measuring means 2 of the apparatus 1 to be easily introduced into a target area of the brachytherapy, the dose measuring means 2 of the apparatus 1 is arranged on a wire-type or hose-type retaining means 4, here a hose-type retaining means. The hose-type retaining means takes the form of a catheter or a cannula. While in the apparatus 1' two dose measuring means 2 and 2' and one radiation means 33 are disposed on a wire-type or hose-type retaining means, in the apparatus 1 only one dose measuring means 2 is disposed on a wire-type or hose-type retaining means 4. The measured values of the dose measuring means 2 of the apparatus 1 are likewise provided by way of the transmission means 3, here an electrical line, to the processing unit 20. The processing unit 20 is also designed to receive the at least one threshold value and to compare it with the measured values which are provided by the apparatuses 1 and 1'. This makes it possible to compare the measured values of the radiation dose which are conditional on the radiation means 33 with predeterminable threshold values. The predeterminable threshold values can be determined for example by measuring sequences or by physical-mathematical models of the object under treatment and the characteristics of radiation means 33 and dose measuring means 2 and 2'. The threshold values can for example specify values at which tissue is likely to be damaged. The threshold value or threshold values can be received for example by inputting on an input means 21 such as a computer keyboard. The difference between measured radiation dose and threshold value can be output for example at an output means 24, such as a computer monitor. It is further conceivable, if the threshold value is exceeded, for an optical and/or acoustic warning to be output to warn a user of a system for supporting brachytherapy that the threshold value has been exceeded.

FIG. 5 shows a schematic diagram of an exemplary embodiment of a system 100 for supporting a brachytherapy with an imaging apparatus 101. Once again a brachytherapy for radiotherapy of a target object 32, here a tumor, is carried out on an object under treatment 30, here a human patient. To this end an applicator 35, here in the form of a catheter, is introduced into a target area 31, which at least includes the target object 32. By means of the applicator 35 a radiation means 33, here a seed, consisting of a radionuclide, or also a miniaturized low-energy x-ray emitter, can be bought into the immediate vicinity of the target object 32. The radiation means 33 emits high-energy radiation, indicated in FIG. 5 by lines 34 which penetrate the target object 32. The system 100, which comprises an apparatus 1 for supporting a brachytherapy and a processing unit 20, here a computer, serves to support the brachytherapy. The apparatus 1 for supporting a brachytherapy comprises a dose measuring means 2 which is introduced into the target area 31 and which is designed to measure the radioactive radiation 34 of the radiation means 33 which is likewise introduced into the target area 31 of the object under treatment 30 and to provide the measured values by means of a transmission means 3, here connected via an electrical line, to the processing unit 20. With the aid of the dose measuring means 2 the radiation 34 emitted by the radiation means 33 can thus be measured directly in the vicinity of the object under treatment 32, in order to guarantee a more precise dose administration and dose monitoring compared to the radiation distribution only predicted in previous methods. The measured values are transmitted via the transmission means 3 to the processing unit 20. The system 100 for supporting a brachytherapy further comprises an imaging apparatus 101 known per se, here an x-ray apparatus, which is designed to obtain at least one image 22 of the radiation means 33, of the dose measuring means 2 and of the target object 32 and provide it to the processing unit 20. The x-ray apparatus, which is embodied as a C-arm x-ray device, has a C-arm 102, on which an x-ray source 103 and an x-ray detector 104 are disposed positioned opposite one another. The object under treatment 30, here a human patient, lies on a support device not shown in the Figure, e.g. an examination table. The image provided by the imaging apparatus 101 can be transmitted to the processing unit 20 by way of a transmission means 105 between imaging apparatus 101 and processing unit 20. The image 22 provided can preferably be displayed on an output means 24 such as a computer monitor, in order to give the user of the system 100 an insight into the local position of radiation means 33, dose measuring means 2 and target object 32. In addition or as an alternative the image 22 can also be further processed by the processing unit 20. For example the processing unit can be designed to determine from the image 23 the positions of the radiation means 33, the dose measuring means 2 and the target object 32, and to determine from the positions a spatial distribution 23 of the radiation dose conditional on the radiation means 33. Using image processing algorithms known per se, especially for medical images, at least the position of radiation means 33, dose measuring means 2 and target object 32 can be determined from one or more images of the imaging device 101. A spatial distribution 23 of the radiation dose which is conditional on the at least one radiation means 33 can be determined from this. Preferably the duration of the radiation 23 and/or the radiation power of the radiation means 33 are included in the determination of the spatial distribution of the radiation dose. Especially advantageously the spatial distribution 23 of the radiation dose is visualized on an output means 24, e.g. a computer monitor. For this purpose the values of the spatial distribution 23 can be visualized by colors, wherein preferably green colors are used for a low radiation amount through to red colors for a high radiation amount. It is also useful for the positions of radiation-sensitive organs to be known for the said objects and for their radiation load, possibly also weighted in accordance with their radiation sensitivity, to be determined and visualized on the output means 24. Through this presentation a user, e.g. a radiologist or oncologist, obtains a good insight into the effectiveness but also possibly critical arrangements during a brachytherapy. An input means 21, here a computer keyboard, serves to control the system 100, for example the type of display of visualizations on the output means 24 or the movement of the imaging apparatus 101.

Finally FIG. 6 shows an example of an inventive method 200 for supporting a brachytherapy with a previously described system, wherein at least one dose measuring means, which is introduced into a target area of an object under treatment including at least one target object, measures radioactive radiation of at least one radiation means, which is introduced into the target area of the object under treatment, and provides the measured values by way of a means of transmission to a processing unit. The method 200 comprises the method steps S1 to S6. It begins with method step S1 and ends "End" after method step S6. The individual method steps are as follows:

Figure 1:
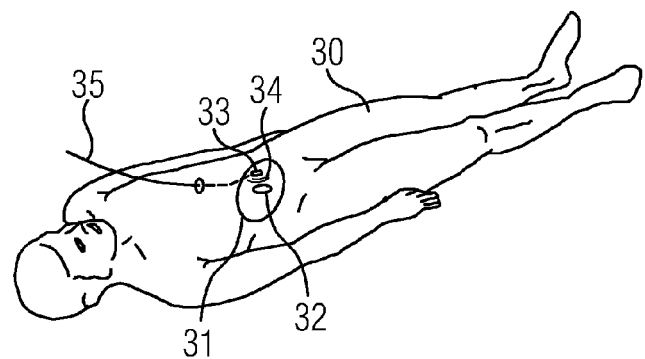
FIG. 1 shows a diagram for describing a brachytherapy according to the prior art.
Figure 2:
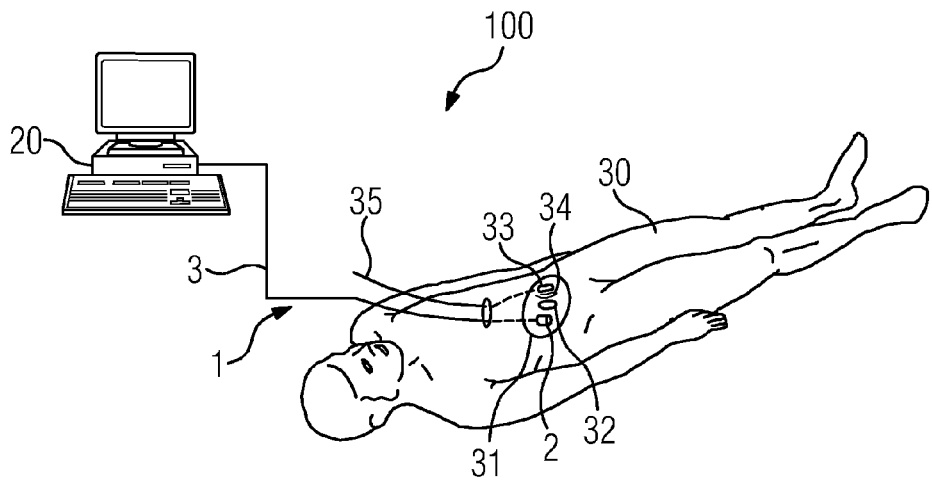
FIG. 2 shows a diagram for describing an exemplary embodiment of a systems for supporting a brachytherapy.
Figure 3:
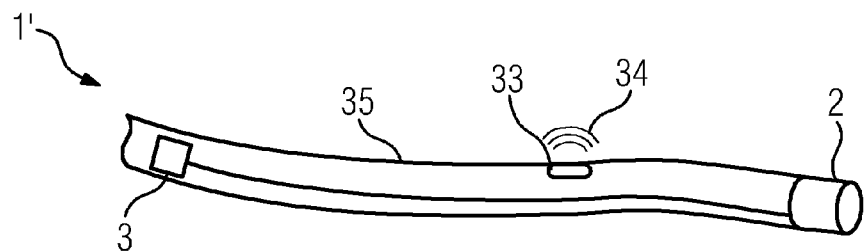
FIG. 3 shows a schematic diagram of an exemplary embodiment of an apparatus for supporting a brachytherapy.
Figure 4:
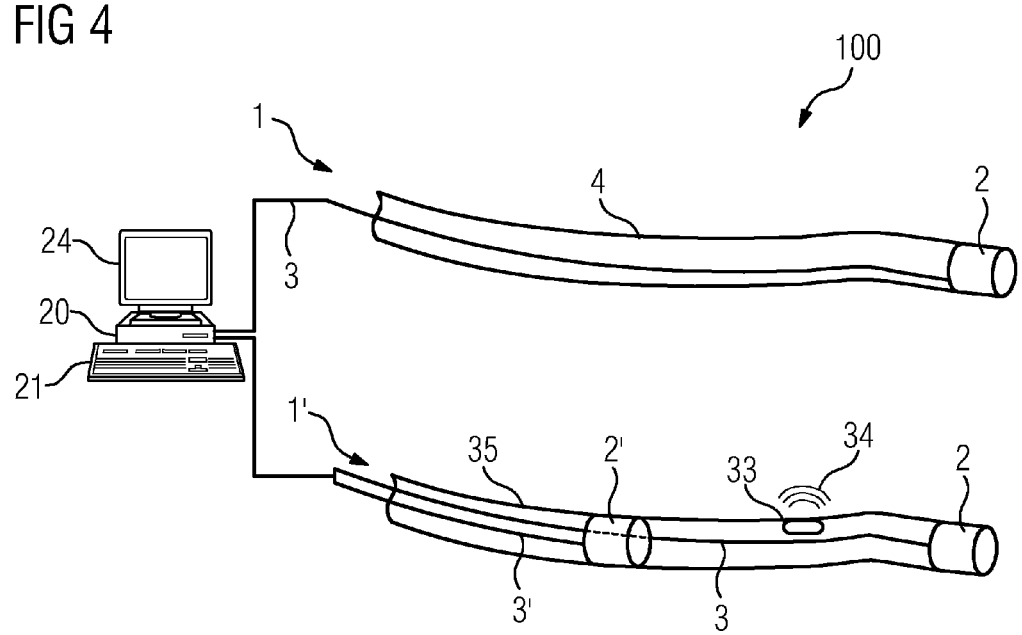
FIG. 4 shows a schematic diagram of a further exemplary embodiment of a system for supporting a brachytherapy with two different apparatuses for supporting a brachytherapy.
Figure 5:
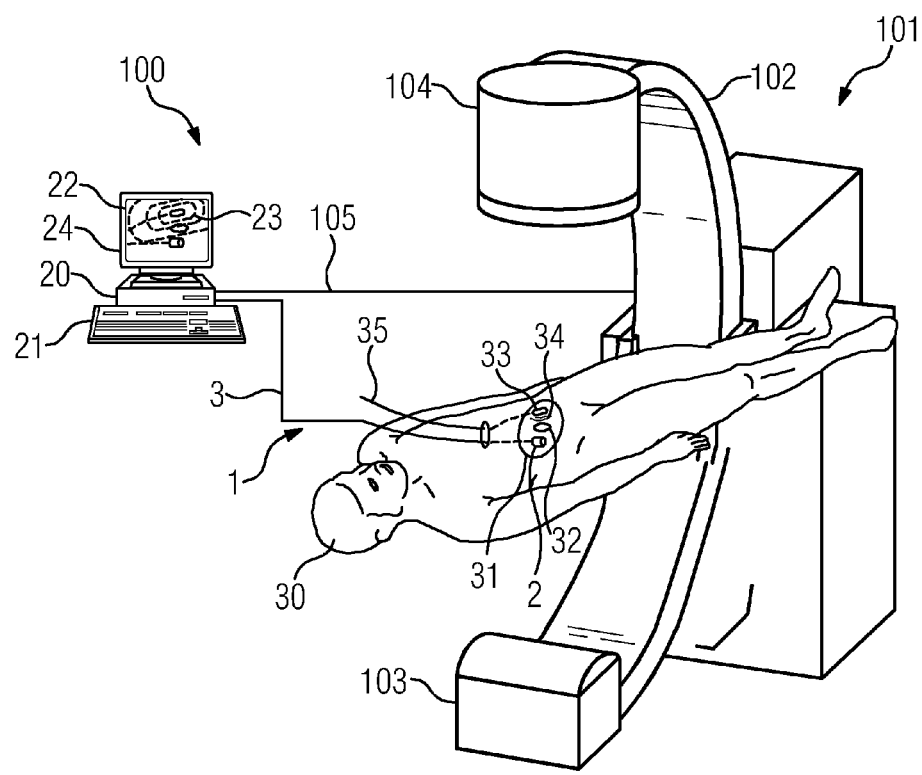
FIG. 5 shows a schematic diagram of an exemplary embodiment of a system for supporting a brachytherapy with an imaging apparatus.
Figure 6:
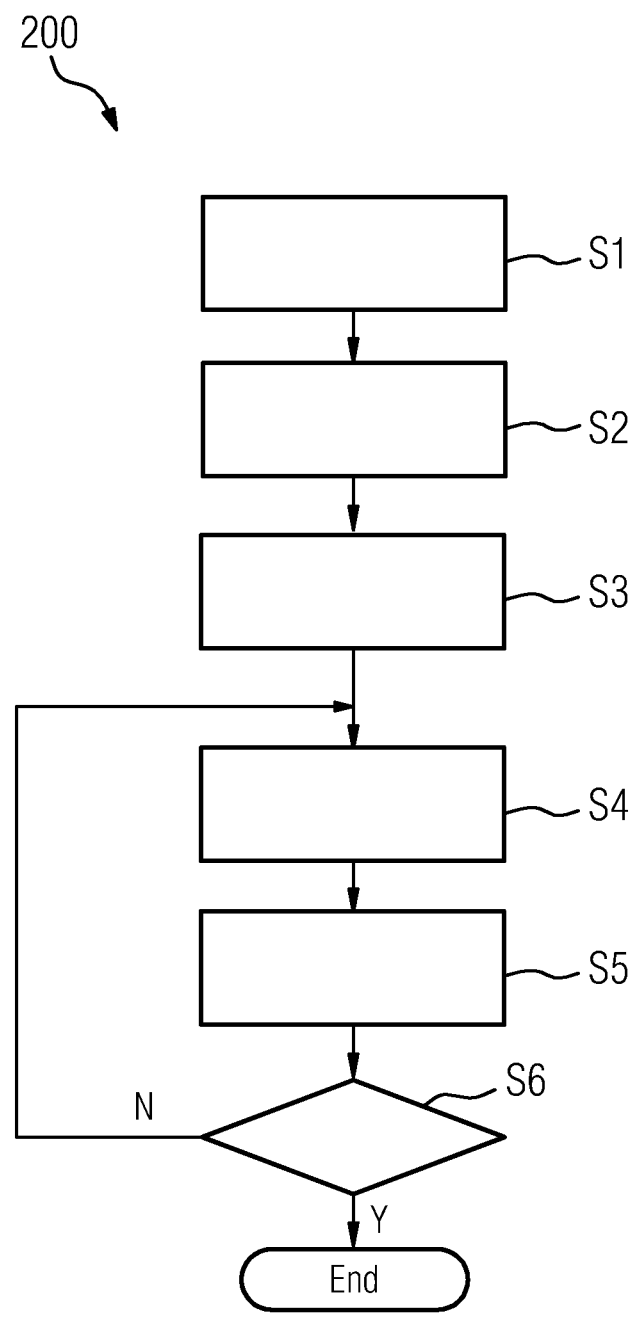
FIG. 6 shows an example of a flow diagram of an inventive method for supporting a brachytherapy.

S1) Recording an image of the at least one radiation means, the at least one dose measuring means and the at least one target object with the aid of the imaging apparatus and transmission of the image to the processing unit;

S2) Determining the positions of the at least one radiation means, the at least one dose measuring means and the at least one target object;

S3) Measuring radioactive radiation of the at least one radiation means with the aid of the at least one dose measuring means;

S4) Determining the spatial distribution of the radiation dose conditional on the at least one radiation means.

S5) Comparing the spatial distribution of the radiation dose conditional on the at least one radiation means with a predeterminable spatial distribution.

S6) Checking an abort criterion and branching to method step S4 if the abort criterion is not fulfilled, else ending, "End", the method.

Preferably the duration of the radiation and/or the radiation power of the radiation means are included in the determination of the spatial distribution in method step S5. Especially advantageously the spatial distribution of the radiation dose is visualized on an output means, e.g. a computer monitor. For this purpose the values of the spatial distribution can be visualized by colors, wherein preferably green colors are used for a low radiation amount through to red colors for a high radiation amount. It is useful if, for the said objects, the positions of radiation-sensitive organs are also determined and for their radiation load are possibly weighted, determined and visualized in accordance with their radiation sensitivity. Through this presentation a user, e.g. a radiologist or oncologist, obtains a good insight into the effectiveness but also possibly critical arrangements during a brachytherapy. At least the measurement of the radioactive radiation of the at least one radiation means is executed repeatedly until the abort criterion is fulfilled. An abort criterion can for example be the reaching of a predeterminable number of method passes, the reaching of a predeterminable duration or the actuation of a key, e.g. on an input means such as a computer keyboard, or the actuation of a switch. If the abort criterion is not fulfilled, at least the measurement of the radioactive radiation of the at least one radiation means is repeated. As an alternative there can also be a branch to method step S1.

A few aspects and exemplary embodiments of the invention will be repeated in summary. In the brachytherapy so-called applicators are introduced into the tumor to be treated or into the tumor tissue to be treated. These applicators are mostly hollow vessels, into which a radiation source, the so-called seed is pushed via a so-called afterloading device and, after a defined duration, is pulled out again fully or in some cases in stages. This enables a previously calculated dose distribution in the tumor to be achieved. Previously the dose to be applied to a tumor has been calculated by a dose planning system before the introduction of the applicator or the applicators. The exposure time of the radiation source in the respective different applicators is produced from the calculated dose. The exposure time and also the calculated applied dose are documented. A great disadvantage of the previously used method of brachytherapy lies in the fact that the applied dose is only calculated, but not really measured. In an exemplary embodiment of the invention, for more precise dose administration and dose monitoring, one or more dose measuring facilities, e.g. one or more dose measuring chambers is applied at specific, predefined points in or on the respective applicators. The result is a precise measurement of the dose in, on or around the tumor region. The dose can be measured and monitored, in order on the one hand to achieve the greatest possible success in the therapy and irradiate the tumor region as well as possible in respect of the local resolution, i.e. the spatial distribution of the dose and energy content. On the other hand adjoining, sensitive organs are to be protected. These sensitive organs, such as e.g. intestine, bladder, because they are directly adjacent to tumors, will necessarily be irradiated, but the load will justifiably be kept within narrow boundaries. Constant monitoring helps to avoid threshold values for sensitive organs being exceeded.

The invention claimed is:

1. A method for supporting a brachytherapy comprising steps of:
    introducing at least one radiation means and at least one dose measuring means into a target area of an object under treatment including at least one target object;
    measuring a value of a radioactive radiation originating from the at least one radiation means using the at least one dose measuring means;
    transmitting the measured value to a processing unit;
    receiving an image obtained from an image apparatus by the processing unit, wherein the image includes the at least one radiation means introduced into the target area, the at least one dose measuring means introduced into the target area, and the at least one target object;
    determining a position of the at least one radiation means introduced into the target area, a position of the at least one dose measuring means introduced into the target area, and a position of the at least one target object from the received image;
    determining a local distribution of a radiation dose of the at least one radiation means from the measured value, wherein the local distribution is determined on the determined position of the at least one radiation means and the determined position of the at least one dose measuring means that are introduced into the determined position of the target area;
    comparing the determined local distribution of the radiation dose of the at least one radiation means with a predeterminable local distribution;
    outputting a warning signal if the determined local distribution exceeds the predeterminable local distribution;
    checking whether an abort criterion is fulfilled; and
    repeating the steps from the measurement of the value of the radioactive radiation until the abort criterion is fulfilled.

2. The method as claimed in claim 1, wherein a duration of the radiation and/or a radiated power of the radiation means are included in the determination of the local distribution of the radiation dose.

3. The method as claimed in claim 1, wherein the local distribution of the radiation dose is visualized on an output means.

4. The method as claimed in claim 1, wherein the method is executed automatically.

5. The method as claimed in claim 1, wherein the abort criterion comprises a predetermined number of passes, a predetermined duration of the radiation, an actuation of a key on an input device, and an actuation of a switch.

* * * * *